(12) United States Patent
Williams

(10) Patent No.: US 6,513,370 B1
(45) Date of Patent: Feb. 4, 2003

(54) WEAR INDICATOR FOR SPORTS BALLS

(75) Inventor: Aaron Williams, Parker, CO (US)

(73) Assignee: Mark Helton, Highlands Ranch, CO (US); part interest ( * ) Notice: Subject to any disclaimer, the term of this patent is extended or adjusted under 35 U.S.C. 154(b) by 0 days.

(21) Appl. No.: 09/062,042

(22) Filed: Apr. 17, 1998

(51) Int. Cl.$^7$ ............................ B23Q 17/04; G01N 5/02
(52) U.S. Cl. ............................................. 73/104; 73/78
(58) Field of Search ............................. 73/78, 86, 104, 73/105, 865.8

(56) References Cited

U.S. PATENT DOCUMENTS

| | | | |
|---|---|---|---|
| 2,020,612 A | 11/1935 | McGrath et al. ............... | 273/61 |
| 2,023,673 A | 12/1935 | Ellis ............................ | 273/61 |
| 4,524,614 A | 6/1985 | Leunig et al. ................. | 73/147 |
| 4,774,150 A | 9/1988 | Amano et al. ............... | 428/690 |
| 5,291,774 A | 3/1994 | Putnum, Jr. .................... | 73/82 |
| 5,303,574 A | 4/1994 | Matossian et al. ............... | 73/7 |
| 5,322,031 A | 6/1994 | Lerner et al. ................ | 116/208 |
| 5,388,331 A * | 2/1995 | Doroodian-Shoja Siamak ....................... | 30/41.7 |
| 5,584,767 A * | 12/1996 | Picchietti et al. ........... | 473/130 |
| 5,603,161 A * | 2/1997 | Welsh ......................... | 30/41.7 |
| 5,997,405 A * | 12/1999 | Russell et al. .............. | 473/140 |

* cited by examiner

Primary Examiner—Max Noori
(74) Attorney, Agent, or Firm—John E. Reilly

(57) ABSTRACT

A wear indicator is provided for use on sports balls and other articles of manufacture, the wear indicator consisting of one or more dots imprinted upon the surface of the article, each dot manifesting a different degree of resistance to wear due to article use and each dot being composed of a mixture of pigment and a rubber cement hardener in which the resistance to wear is proportional to the ratio of the hardener to the pigment, or in which each dot is of a selected thickness and wear resistance proportional to its thickness. A brand name also may be imprinted on the surface of the article either as a permanent marking or to signify a predetermined degree of wear when no longer visible to the eye.

17 Claims, 1 Drawing Sheet

WEAR INDICATOR FOR SPORTS BALLS

BACKGROUND AND FIELD OF THE INVENTION

This invention relates to wear indicators, and more particularly to a novel and improved method and means for indicating when a sports ball, such as, a racquetball, as well as other articles, has been worn past its useful life; and still further relates to wear dots for indicating when a sports ball has reached each of successive degrees of wear during its life.

Many balls used in various sports have a useful life span. When a ball has been enjoyed to the end of its useful life, it begins to show signs of wear and tear. Severe wear marking the absolute end of the ball's life may be manifested by splits, cracks, or ruptures in the ball. Before failing completely, however, a ball may show signs of wear that perceptibly impair the ball's performance, such as reduced resiliency resulting in diminished "bounce." Also, irregular, "off balance," eccentric, or other non-standard shapes resulting in imperfect bounces, rolls, and the like, which can detract from the enjoyment of the game. The problem of worn balls afflicts all sports that use balls, including baseball, football, basketball, and soccer. The problem is most acute, however, in the racquet sports, such as tennis, racquetball and squash, where an even mildly "flat" or odd ball can dramatically affect the quality of play. Nearly all racquetballs tend to deform or lose bounce after significant use.

Unless a ball is nearly new, there is no reliable manner for simply and quickly evaluating its degree of wear. Very new balls may still exhibit the manufacturer's printed brand name, but brand names are printed using ephemeral inks that wear off in as few as two or three games. The brand names are printed on the balls primarily to trademark the balls for identification at the time of purchase. Nevertheless, racquetball manufacturers sometimes use the printed brand name as a usage gauge for purposes of warranty; if a ball splits or breaks before the printed brand name has worn off, the ball is regarded as "under warranty" and perhaps the subject of free replacement. Most balls have significant useful life remaining after the label is gone. Simple visual inspection of a ball presently known in the art is an inadequate means of determining remaining useful life. Some balls exhibit a scuff or two and may remain quite lively and symmetrical and completely acceptable for continued use. Contrariwise, a used ball can appear unimpaired and nevertheless have lost much of its resiliency or roundness.

Currently, the most common methods for determining if a used ball is satisfactory for further play are subjective and imprecise. Probably the most often used "wear test" is to drop to the floor, from a height of about five feet, the used ball simultaneously alongside a "fresh" ball to compare the respective bounce of the balls. Experienced players sometimes simply drop the one ball to be evaluated to observe the bounce and evaluate based on experience. Many players also squeeze the ball in the hand to sense rigidity and regularity. Another very common practice is to hit the balls with a racquet to "test" the feel of the ball. Irregular or poor rebounds indicates that a ball has been used past its prime and is a candidate for discard. These known methods of ball evaluation suffer from a number of drawbacks. All are time-consuming, and realistically can be performed on but one ball at a time. The drop-and-compare test demands the availability of a fresh, new, "control" ball to serve as the standard. All the tests can be affected by ball temperature and are generally unscientific and subjective.

Thus, at any given time, a racquetball sports person is at best only vaguely aware of the degree of wear of any particular used ball in his or her possession. Consequently, many players, especially recreational players, continue to use balls worn past their prime and to the point that playing performance may be affected. Also, players may overcompensate by hitting a "dead" ball harder, possibly causing injury. Moreover, depending upon the level of play, such as, tournament or professional play, it is desirable to be able to ascertain the degree of wear at different stages throughout the useful life of the ball.

Accordingly, there is a need for a simple, accurate means for evaluating the degree of usage or wear that a ball has undergone in order to eliminate from play those balls that have exceeded their useful life. An ideal method of evaluation will permit a ball's degree of wear to be determined by visual inspection of the ball, so that several balls can be evaluated or compared simultaneously and without the use of a new "control" or "standard" ball. Also desirable is a ball wear indicator that signals various degrees of ball wear, so that a user can at a glance tell if, for example, the ball is nearly new, or well-used but still acceptable for play, or over-worn and in need of retirement.

Similarly, a need remains for a means for imprinting a ball with a lasting manufacturer identification. Ball users need a way to sort used balls according to manufacturer in order to reserve particular brands of balls for appropriate situations, such as expensive balls for tournament play, cheaper balls for use on poor quality courts, and the like. Moreover, ball manufacturers seek to present their trademark to the user throughout the ball's useful life, rather than merely for the first two or three games.

Patents representative of the prior art are U.S. Pat. Nos. 2,020,612 to J. T. McGrath et al; 2,023,673 to D. W. Ellis; 4,524,614 to C. V. Leunig et al; 4,774,150 to K. Amano et al; 5,291,774 to C. E. Putnam, Jr.; 5,303,574 to J. Matossian et al and 5,322,031 to M. Lerner et al.

SUMMARY OF THE INVENTION

It is therefore an object of the present invention to provide for a novel and improved wear indicator for articles of the type in which the useful life is dependent upon the wear to which its external surface is exposed.

It is another object of the present invention to provide for a novel and improved wear indicator for sports balls and other articles which is low cost, simple and efficient to apply to the ball or other article and yet highly reliable and dependable in use.

It is a further object of the present invention to provide for novel and improved marking elements to be applied to sports balls and the like to indicate different degrees of wear to which the ball is subjected.

It is a still further object of the present invention to provide for a novel and improved wear indicator for articles which does not require modification to the article itself or alteration of the article in the course of manufacture; and further wherein use of the wear indicator enables imprinting of a more lasting manufacturer's identification mark on the article.

In accordance with the present invention, there has been devised a novel and improved wear indicator for use in combination with various articles of manufacture which have a useful life dependent upon the wear to which their external surfaces are exposed in use and wherein the novel and improved wear indicator comprises a plurality of visible marking elements applied to each of the exposed surfaces, each of the elements being characterized by possessing a different selected degree of wear, or resistance to wear so as to indicate that the article has been subjected to a predetermined degree of wear when that marking element is no longer visible to the human eye.

The invention is further characterized by establishing different degrees of wear according to the thickness of each marking element, composition of the marking element, or a combination of both so that each respective marking element will signify a selected degree of wear when no longer visible to the human eye. Furthermore, each different marking element is of a different color, each color signifying a selected or different degree of wear.

The present invention has particular utility when used in connection with sports balls and in particular those composed of a rubber or rubber-like material which are susceptible to wear in relation to their extent of use, and a preferred form of wear indicator is composed of a mixture of pigment and rubber cement hardener in which the resistance to wear increases with increases in the volumetric ratio of the hardener to the pigment. Moreover, the marking elements are preferably in the form of dots and may be used alone or in combination with a brand name on the ball to signify different selected degrees of wear.

The above and other objects, advantages and features of the present invention will become more readily appreciated and understood from a consideration of the following detailed description of preferred and modified forms of the present invention when taken together with the accompanying drawings in which:

DETAILED DESCRIPTION OF THE PREFERRED EMBODIMENT

In this disclosure the term "ball" shall mean any ball used in play or sports activity, and "racquetball" refers to a ball adapted for use in a particular sport requiring the use of a paddle or racquet, including but not limited to racquetball, tennis, handball, table tennis or squash. The present invention finds particular application in the field of racquet sports, but a person of ordinary skill in the art will readily appreciate that the invention may find beneficial use in other ball sports such as volleyball, soccer, basketball, or the like, and indeed may be applicable inside or outside the field of sporting goods generally.

Figure 1:
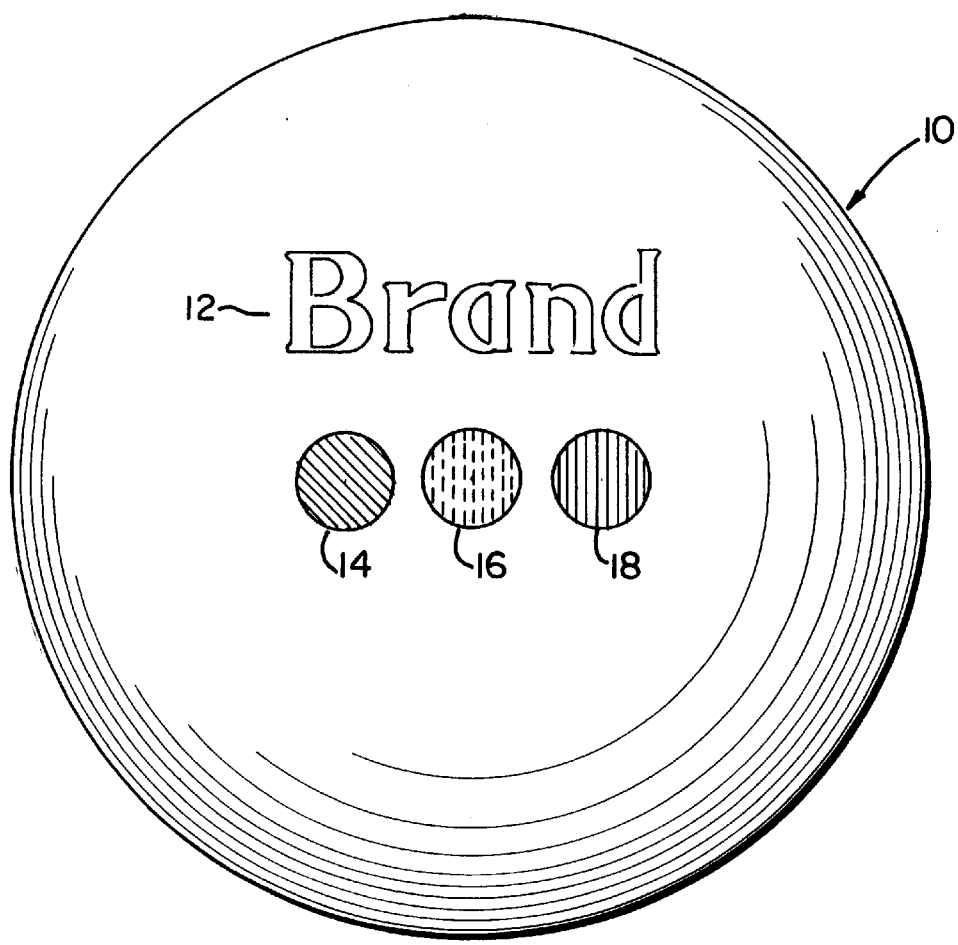
FIG. 1 is a view in elevation of a racquetball showing the wear indicator of a preferred embodiment of the invention.

Referring to FIG. 1, there is seen a racquetball 10, such as a racquetball, with the wear indicator system of the present invention. The racquetball 10 is fashioned from conventional materials, as the present invention advantageously does not demand any significant modifications to the known processes for manufacturing the body of the ball 10 or the compositions from which the body of the ball 10 is formed. The typical racquetball is made from elastomeric rubber composition, and has a lightly textured surface. Squash balls are smooth-surfaced. The preferred composition of the ball 10 provides some porous texture characteristics, but the invention is suitable for use with smooth-surfaced balls.

The ball 10 has printed thereon, according to the present invention, a trademark 12 or other manufacturer's indicia consisting of, for example, a logo, a logo and text, or, as illustrated, a textual brand name. The trademark 12 is imprinted upon the ball 10 as permanently as possible as herein described, but does not affect the behavior of the ball 10.

Also imprinted upon the racquetball 10 according to the invention is at least one, and preferably three as indicated, wear indicator spots or dots 14, 16, 18. Dots may be substantially adjacent to the trademark 12, or can be located elsewhere upon the exterior surface of the ball 10. The indicator dots 14, 16, and 18 preferably are grouped together in one location upon the ball 10, but alternatively may be spaced about at different locations upon the exterior of the ball 10.

In the preferred embodiment of the invention, the dots are differently colored. For instance, the preferred embodiment features a first dot 14 colored green, a second dot 16 colored yellow, and a third dot 18 colored red. Additionally, each of the dots 14, 16, 18 is subject to a different rate of physical wear, so that, for instance, the first dot 14 wears off the ball 10 faster than the second dot 16, and the second dot 16 faster than the third dot 18. The three dots thus are color-coded to serve both individually and collectively as indicators of ball wear.

Typically, the first dot 14 may wear off quickly, e.g., approximately as rapidly as the manufacturer's brand name printed with the ink currently in use in the industry. Thus, the first dot 14 may show signs of wear immediately upon use of the ball 10, and nearly vanishes from view after, for example, approximately 30 to 120 minutes of play. The first dot 14 when still visible upon the ball 10 accordingly indicates that the ball is nearly new. First dot 14 may serve the second function of signaling warranty expiration, i.e., if the first dot 14 has worn completely off, the manufacturer would no longer replace a fractured ball free of charge.

The second dot 16 is more resistant to wear than the first dot 14, and visibly endures two to three times as long as the first dot 14. Thus, the second dot 16 preferably wears completely from the exterior surface of the racquetball 10 after the ball has been used for approximately two to four hours of constant play, most preferably after approximately three hours of constant usage. After the disappearance of the first dot 14, the second dot 16, while still visible upon the racquetball 10, indicates that the ball is no longer fresh and new but is adequate for use.

The third dot 18, is most resistant to wear. When the third dot 18 begins to manifest signs of wear, the ball 10 is approaching the end of its useful life. A significantly worn third dot 18, particularly when the second dot 16 has worn completely off, indicates an immediate need to discard the ball 10.

The inks utilized to practice the invention preferably are non-chipping, temperature resistant and flexible, and are absorbed to differing degrees by the surface of the ball 10. The higher the proportion of hardener used, the more the ink is absorbed into the surface. A "super glue" hardener initially acts as a solvent, assisting the ink in penetrating and to a degree actually mixing with the surface material of a rubber ball 10. In the case of fabric-covered balls such as tennis balls, the pigment-to-hardener ratio will affect the depth to which the pigment is absorbed into the fabric, thus affecting the permanency of the mark..

Accordingly, in the preferred embodiment, ink is transferred to one or more, preferably three, dots such that the wearing of the ink indicates the amount of life remaining in the ball 10. The dots 14, 16, 18 are preferably, in the case of a conventional racquetball, approximately three-thirty seconds (3/32) of an inch (approximately 2.4 mm) in diameter, large enough to be easily seen but not so weighty as to interfere with the behavior of the ball while in play, nor large enough to create a significant area of different texture (e.g., smoother or rougher than normal ball surface).

Figure 2:
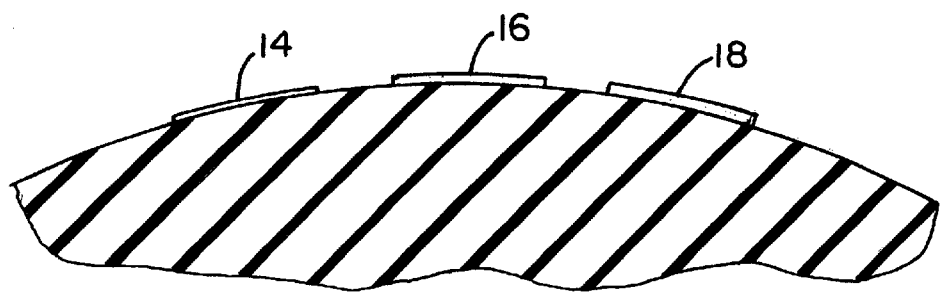
FIG. 2 is an enlarged sectional view of the ball shown in FIG. 1.

Combined reference is made to FIGS. 1 and 2. In one preferred embodiment of the invention, the first dot 14 is applied as a single coat of ink to the surface of the racquetball 10. The preferred ink for the imprinting of the first dot 14 is MARKEM® 5461 brand air dry pad printing ink, available from MARKEM Corporation, 2340 Bering Drive, San Jose, Calif. The ink preferably is applied to the ball 10 to a thickness of approximately one two hundred and fifty-sixth of an inch (1/256") (approximately 0.01 mm) using a MARKEM® Model 596 closed reservoir pad printer employing a 4-inch cup. The ink is applied using a single strike, and the machine cycle rate may be as high as 20 cycles per minute.

The second dot 16 preferably is printed onto the racquetball 10 using a pigment mixed with a hardener. An acceptable pigment is an acrylic paint available under the trademark "CERAMCOAT" from Delta Technical Coatings, Inc., Whittier, Calif. Prior to application, the pigment is thoroughly mixed with a rubber cement hardener, such as BEST-TEST White Rubber Paper Cement available from Union Rubber, Inc., Trenton, N.J. Such a hardener includes natural rubber, as well as hexane and petroleum ether resins. The pigment is mixed in a ratio of 3 parts by volume of rubber cement to one part by volume of pigment, and applied to the ball to a thickness of approximately one-hundred twenty eighth of an inch (1/128") or approximately 0.025 mm. The preferred manner of application is by brush, although alternative known application methods may be used. The pigment-cement mixture produces a second dot 16 that wears completely after substantial use, but nevertheless outlasts the first dot 14.

The third dot 18 also is applied upon the racquetball 10 preferably by pad printing. The third dot 18 is imprinted using an ink-hardener mix comprising a higher volumetric ratio of hardener. We have determined that the third dot 18 is best applied to a thickness of about one one-hundredth of an inch (1/100"), or approximately 0.04 mm, using Organic Products F-150 ink thoroughly mixed with Ross® brand "super glue" in a volumetric ratio of 25 parts ink to one part glue.

In the preferred embodiment, the trademark 12 is pad printed using substantially the same ink-hardener mix as used to apply the third dot 18. The trademark 12 consequently remains visible throughout the useful life of the ball 10. The wear resistance of a particular dot can be controlled at the time of application by adjusting the ink-to-hardener ratio. In all instances, the ink may be dyed to provide variety of color.

A desirable alternative process for mass-producing the invention is the incorporation of the dots 14, 16, 18 into the surface of the ball 10 at the time the ball is manufactured. In factory production, the inventive ball may be mass-produced by pre-mixing the same rubber used to make the ball with a pigment. The pigmented mix, optionally in the form of a dry powder, is then put into the ball mold, followed by the remaining material to form the complete ball. As a result of the molding process, a colored dot with a thickness of about 1/64" is formed on the outside of the ball.

Alternative embodiments of the invention abound. For instance, if multicolored dots 14, 16, 18 elevate manufacturing costs above the costs desired for "medium quality" balls, three dots of one color but graduated wear resistance may be applied. The individual dots may be in a row, or arranged in patterns or arrays upon the ball 10. An alternative embodiment may also include a single bar or stripe of graduated resistance and/or color along its length. Additionally, other embodiments may employ the substantially permanently imprinted trademark 12 in lieu of the high-wear third dot 18.

Accordingly, there is provided by the present invention a ball that encourages players to retire the ball prior to, or at least at the time of, the ball's reaching the limit of its useful life or performance. A player may take one or more balls in hand and upon visual inspection immediately objectively evaluate the degree of wear. The player may then judge whether to place the ball in play. There is also provided by this invention a means for permanently branding a ball by imprinting the ball with a brand name using the most durable of the marking compositions provided. All players may readily identify the ball by manufacturer, regardless of the age or wear of the ball.

The invention offers the advantage of player convenience, as well as promoting new ball purchases, an advantage to manufacturers. A player may differentiate his or her ball from that of his or her competitors, or select a used ball for a particular occasion, based upon brand name without regard for ball-wear. A player's ball is more personalized, as the invention changes a ball from an item that quickly becomes nameless and generic through use on the court to something that builds brand equity from the moment of purchase to the time of discard.

Furthermore, with the provision of permanent markings upon the ball, expert racquetball players may find that they can adopt the technique, known in tennis, of concentrating on the ball by "looking for the trademark." Thus, a player desiring to improve eye contact with a ball in play may prefer a permanently marked ball. In any event, beginner players are likely to discontinue the practice, currently commonly encountered, of playing games with worn-out balls.

It will be evident that the relative thicknesses given for the dots 14, 16, and 18 are for the purpose of illustration and not limitation and may vary according to the wear characteristics of the ball or other object as well as the type of ink or pigmentation employed. Further, the person of ordinary skill in the art will appreciate that the present invention may find beneficial use outside the field of sports balls. The present imprinted wear indicator invention may be utilized upon gloves, grips, shoes, and the like, anywhere a user may wish to have a reliable means for gauging otherwise imperceptible wear prior to the expiration of an item's useful life.

It is therefore to be understood that while preferred and alternate forms of invention are herein set forth and described, the above and other modifications and changes may be made therein without departing from the spirit and scope of this invention as defined by the appended claims and reasonable equivalents thereof.

I claim:

1. In a sports ball having an external surface susceptible of wear in relation to its extent of use, a wear indicator on said surface defined by a plurality of marking elements, each of said elements being of a different thickness so as to have a different predetermined degree of resistance to wear in relation to use of said ball so as to signify different selected degree of wear when each respective of said marking elements is no longer visible to the human eye.

2. In a sports ball according to claim 1 wherein said marking elements are disposed in spaced relation to one another.

3. In a sports ball according to claim 2 wherein each of said marking elements is of a different color, each said color signifying a different selected degree of wear of said sports ball when said color is no longer visible to the eye.

4. In a sports ball according to claim 2 wherein each of said marking elements is composed of a mixture of pigment and hardener.

5. In a sports ball according to claim 4 wherein the useful life of each said element increases with the volumetric ratio of hardener to pigment present in each said element.

6. In a sports ball according to claim 2 wherein each of said marking elements is defined by a dot, said dots being disposed in spaced relation to one another.

7. In a sports ball according to claim 6 wherein said dots are arranged in a single row.

8. In a sports ball according to claim 2 wherein one of said marking elements is defined by a manufacturer's brand name or trademark imprinted on said surface.

9. In a sports ball having an external surface susceptible of wear in relation to its extent of use, a wear indicator on said surface defined by at least one visible marking element having a predetermined degree of resistance to wear in relation to use of said ball so as to become invisible after said ball is exposed to a predetermined degree of wear, wherein each said marking element is composed of a mixture of a pigment and a rubber cement hardener.

10. In a sports ball according to claim 9 wherein each said marking element is applied in a predetermined thickness to said surface.

11. In a sports ball according to claim 9 wherein a plurality of marking elements of different thicknesses are applied to said surface, each of said marking elements having a different degree of wear based on its thickness.

12. In a sports ball according to claim 9 wherein a plurality of marking elements are provided on said surface, each of said marking elements being of a different color.

13. In a sports ball according to claim 9 wherein a plurality of marking elements are provided, each said marking element composed of a mixture of pigment and rubber cement hardener, the volumetric ratio of said hardener to said cement increasing with the degree of wear to be exhibited by said marking element.

14. In a sports ball according to claim 9 wherein said marking element includes a brand name imprinted on said surface, said brand name having a predetermined degree of wear.

15. The method of indicating degree of wear of a sports ball comprising the steps of:
  (a) forming a plurality of different colored dots by intermixing a plurality of different colored pigments with a rubber cement hardener material, the ratio of said hardener to each of said different colored pigments increasing with the degree of wear to be represented by each said color; and
  (b) applying each of said different colored dots to an external surface of said sports ball.

16. The method according to claim 15 wherein said sports ball is composed of a rubber or other material having the characteristic of rubber material.

17. The method according to claim 15 wherein said dots are disposed in spaced relation to one another.

\* \* \* \* \*